(12) United States Patent
Shau

(10) Patent No.: US 8,773,663 B2
(45) Date of Patent: Jul. 8, 2014

(54) LUMINOUS UNIT

(71) Applicant: Vertilas GmbH, Garching (DE)

(72) Inventor: Robert Shau, Munich (DE)

(73) Assignee: Vertilas GmbH, Garching (DE)

( * ) Notice: Subject to any disclaimer, the term of this patent is extended or adjusted under 35 U.S.C. 154(b) by 0 days.

(21) Appl. No.: 13/622,261

(22) Filed: Sep. 18, 2012

(65) Prior Publication Data

US 2013/0027703 A1 Jan. 31, 2013

Related U.S. Application Data

(63) Continuation of application No. PCT/EP2011/054036, filed on Mar. 17, 2011.

(30) Foreign Application Priority Data

Mar. 18, 2010 (DE) .......... 10 2010 003 034

(51) Int. Cl.
*G01J 4/00* (2006.01)
*H01S 5/022* (2006.01)
*G01J 3/427* (2006.01)
*G01N 21/17* (2006.01)
*G01N 21/21* (2006.01)

(52) U.S. Cl.
CPC ............. *H01S 5/02296* (2013.01); *G01J 3/427* (2013.01); *G01N 21/1702* (2013.01); *G01N 21/21* (2013.01)
USPC .......................................... 356/364

(58) Field of Classification Search
CPC .............................. H01S 5/02296; G01J 3/427
See application file for complete search history.

(56) References Cited

U.S. PATENT DOCUMENTS

| | | | |
|---|---|---|---|
| 5,604,636 A * | 2/1997 | Asami et al. .................. | 359/637 |
| 5,637,872 A | 6/1997 | Tulip | |
| 6,069,905 A | 5/2000 | Davis et al. | |
| 6,091,504 A * | 7/2000 | Walker et al. ................. | 356/437 |
| 6,567,435 B1 * | 5/2003 | Scott et al. ............... | 372/29.021 |
| 6,876,685 B2 * | 4/2005 | Umemoto et al. ......... | 372/43.01 |
| 6,963,598 B1 | 11/2005 | Guenther et al. | |

(Continued)

FOREIGN PATENT DOCUMENTS

EP       1783481 A1       5/2007

OTHER PUBLICATIONS

Regalado et al., Polarization Properties of Vertical-Cavity Surface-Emitting Laser, May 1997, IEEE Journal of Quantum Electronics, vol. 33 No. 5, pp. 765-783.*

*Primary Examiner* — Gregory J Toatley
*Assistant Examiner* — Juan D Valentin, II
(74) *Attorney, Agent, or Firm* — Lathrop & Gage LLP

(57) ABSTRACT

A luminous unit for an optical gas detector, an optical gas detector including the luminous unit, and a method of recording an absorption spectrum in an optical gas detector include a light source for linearly polarised light radiation and a housing with an exit window. A wavelength of the light radiation radiated from the light source is tunable. The light source is arranged in the housing such that the main emission direction (OA) of the light source encloses an inclination angle ($\phi$) of between 10° and 50° with a normal (N) to the main extension plane (HE) of the exit window. The direction of polarisation (P) of the light radiation encloses a rotation angle ($\theta$) of between 22.5° and 67.5° with the plane of incidence on the exit window.

18 Claims, 5 Drawing Sheets

(56) References Cited

U.S. PATENT DOCUMENTS

| | | |
|---|---|---|
| 7,045,824 B2* | 5/2006 | Malone et al. .................. 385/92 |
| 7,068,694 B2* | 6/2006 | Yamamoto ................. 372/43.01 |
| 7,113,658 B2 | 9/2006 | Ide et al. |
| 7,439,533 B2* | 10/2008 | Kito et al. ..................... 250/552 |
| 8,199,786 B2* | 6/2012 | Gaillard et al. ................. 372/34 |
| 2005/0265413 A1 | 12/2005 | Tsuda et al. |
| 2010/0002235 A1* | 1/2010 | Willing et al. ................ 356/437 |
| 2010/0054297 A1* | 3/2010 | Wakabayashi et al. ....... 372/103 |

* cited by examiner

LUMINOUS UNIT

RELATED APPLICATIONS

This is a continuation of PCT Patent Application Serial No. PCT/EP2011/054036, filed Mar. 17, 2011, which claims priority to German Patent Application 10 2010 003 034.1, filed Mar. 18, 2010, the disclosures of which are incorporated herein by reference.

BACKGROUND

1. Technical Field

This disclosure relates to a luminous unit for gas detection comprising a light source for linearly polarised light radiation and a housing with an exit window.

2. Discussion of Related Art

A gas sensor and an associated luminous unit are known from EP 1 783 481 A1. To improve the intensity stability it is proposed to tilt the exit window relative to the optical axis or main direction of radiation by the Brewster angle (in this case about 57°). Such a tilt, in linearly polarised laser light in pure p-polarisation, can reduce unwanted back-reflections at the cover.

However, there is still the problem that interference effects occur at the exit window which interfere with the signal that is to be measured. Disruptive optical modulations occur which are manifested for example as fluctuations in the light intensity measured as a function of the wavelength in the photodetectors of measuring apparatus for optical gas analysis. Particularly in an application known by the name "open path gas detection" (OPGD) in which the laser beam is passed over a shorter or longer distance through the space that is to be monitored, fluctuations in the radiation intensity are particularly disruptive as they significantly impair the signal-to-noise ratio. During measurement, in fact, it is generally not possible to distinguish directly between an attenuation caused by absorption in a gas and an attenuation caused by interference effects, which significantly increases the complexity of measurement that is to be carried out and the costs involved.

It would therefore be particularly desirable to provide a tunable luminous unit with a variable wavelength for gas detection in which the wavelength dependency of the light radiation intensity after the exit window is reduced.

SUMMARY

The exemplary embodiments improve the properties of optical apparatus that use polarised light of variable wavelengths. Applications include apparatus with tunable laser diodes for sensing gas using the optical absorption in the gases. Optical gas sensors are essentially based on the principle of infrared (IR) spectroscopy. The volume to be analysed is irradiated with monochromatic light the absorption of which in the volume is determined. By varying the wavelength it is possible to record a spectrum, on the basis of which the gases present can be determined. The detection of gas therefore requires special luminous units which have, for example, particularly high wavelengths stability and mode stability.

According to one aspect, a luminous unit for an optical gas detector is provided. The luminous unit includes a light source for linearly polarised light radiation and a housing with an exit window. A wavelength of the light radiation radiated from the light source is tunable. The light source is arranged in the housing such that the main emission direction (OA) of the light source encloses an inclination angle ($\phi$) of between 10° and 50° with a normal (N) to the main extension plane (HE) of the exit window. The direction of polarisation (P) of the light radiation encloses a rotation angle ($\theta$) of between 22.5° and 67.5° with the plane of incidence on the exit window.

BRIEF DESCRIPTION OF THE DRAWINGS

The foregoing and other features and advantages will be apparent from the more particular description of preferred embodiments, as illustrated in the accompanying drawings, in which like reference characters refer to the same parts throughout the different views. The drawings are not necessarily to scale, emphasis instead being placed upon illustrating the principles of the preferred embodiments. In the drawings, the sizes and thicknesses of layers, regions and features may be exaggerated for clarity.

DETAILED DESCRIPTION

Figure 1:
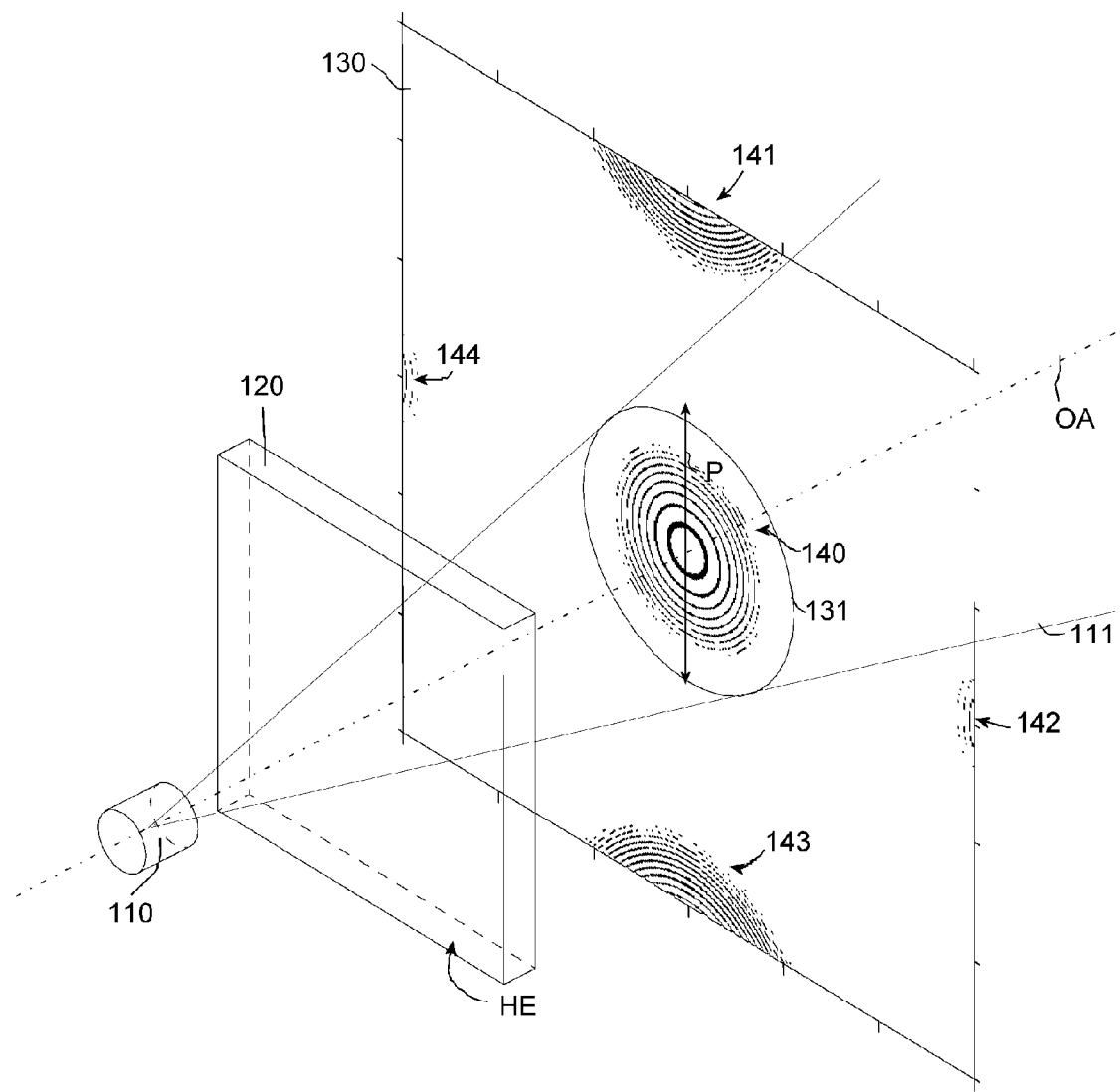
FIG. 1 includes a schematic diagram of a light source, an exit window and the resulting interference pattern when linearly polarised light is perpendicularly incident.

The present disclosure is based on a measure of providing a light source of a luminous unit in a housing comprising an exit window in such a way that the interference effects in the irradiated region of the exit window are kept to a minimum. For this purpose, a correspondingly optimum alignment of the main extension plane of the exit window is selected, on the one hand with respect to the direction of polarisation and on the other hand with respect to the main emission direction of the light radiation. The disclosure thus provides a luminous unit of adjustable or tunable wavelength for gas detection, wherein the wavelength dependency of the intensity of the light emitted from the exit window is significantly reduced. In an alignment according to the disclosure the main emission direction of the light source forms an angle of inclination $\phi$ of preferably 30°±20° with a normal to the main extension plane of the exit window. Moreover, the polarisation direction encloses with the plane of incidence (which, as known, is spanned by the normal to the main extension plane of the exit window and the main emission direction of the light source) a rotation angle $\theta$ of preferably 45°±22.5°.

One particular embodiment relates to a case in which rotation angle $\theta$ of 45°, i.e. s+p-polarisation has occurred. This produces on the one hand particularly effective suppression of the interference effects and, on the other hand, ensures an invariance of the system relative to a 90° rotation of the polarisation plane of the light radiation, which is particularly favourable for manufacture. Thus manufacture is made easier as there are four equally valid possible ways of arranging the housing or the exit window relative to the light source. However, the disclosure also encompasses rotation angles which are located within preferred ranges of 10°, 15° or 22.5° around 45°.

In some embodiments, the angle of inclination φ is between 20° and 40°, preferably between 25° and 35°, particularly 30°. It has been found that in this way a particularly large spectral range can be obtained with low wavelength dependency. Moreover a relatively small inclination angle of this kind is significantly easier to produce than the inclination angles of up to 60° described in the prior art.

The alignment of housing and light source according to the embodiments also reduces the influence of the thickness of the exit window. In the alignments known in the prior art the influence of the interference increases with the thickness of the window. For this reason, particularly thin windows are recommended, but these are expensive to produce, delicate and not very robust. A favourable range, according to the some embodiments, for the thickness of the exit window is between 0.2 mm and 1.5 mm. The thickness is, particularly preferably, at least 1 mm.

Because of the significantly reduced wavelength dependency, luminous units according to the embodiments are particularly well suited to optical gas sensors. During use of a luminous unit according to the embodiments an adsorption spectrum is recorded, in order to detect the presence of gases.

U.S. Pat. No. 7,113,658 B2 discloses a luminous unit which is used for data transmission and is unsuitable for gas detection on account of its lack of wavelength stability and mode stability. Nor can this specification lead the skilled man to the subject matter of the present disclosure as the geometric configuration shown therein is based on completely different considerations and effects. In fact, the geometric configuration is precisely not used to minimise a wavelength dependency. Rather, the tilting of the exit window in the direction of emission serves to couple out some of the light into a monitor diode. The rotation of the exit window ensures that both unstable modes are attenuated equally, so that there is no jump in intensity resulting from mode jumping. Neither cause, i.e., monitor diode and mode instability, is related to the problem on which the present disclosure is based.

It will be understood that the features recited above and those yet to be described hereinafter may be used not only in the particular combination specified herein, but also in other combinations or on their own without departing from the scope of the present disclosure.

Findings on which the description herein is based will be described. A light beam emerging from an aperture, e.g. from a monomodal laser diode or from a monomodal glass fibre, represents, as a good approximation in the far field, a spherical wave with a Gaussian intensity distribution about the optical axis, the intensity distribution generally being elliptical in edge-emitting laser diodes and circular in surface-emitting laser diodes or glass fibres. The beam contains a range of propagation directions which extends in several angular directions, the median direction of propagation or the main emission direction of the beam corresponding to the optical axis.

The following description gives consideration to the transmission of such a beam through a transparent flat sheet of glass, e.g., an exit window, as the beam-forming element, again in the far field. The findings can also be applied to elements with other beam-forming properties such as, for example, transparent lenses or wedges, and to finite spatial distances.

It is known that when a spherical wave passes through a flat sheet of glass, concentric interference rings are formed, known in the specialist literature, for example, as "transmission fringes". The interference rings are formed by the distribution of the incident beam caused by internal reflections at interfaces between volume regions with different refractive indices and superimposition of the partial beams, which occurs more constructively in specific directions of propagation, depending on the refractive index and thickness of the glass sheet and the wavelength and polarisation of the light beam (light regions) and more destructively in other directions of propagation (dark regions). The angular pattern of the interference rings is independent of the distance between the aperture and the glass sheet and independent of surface coatings on the glass, of the kind usually applied in order to influence the surface reflectivity, in particular in order to reduce it (non-reflective coating), while as a rule the absolute contrast of the degree of transmission between constructive and destructive directions of propagation is also reduced when there is a reduction in the reflectivity.

If, in the case of non-polarised light, the optical axis is perpendicular to the main extension plane of the window, the interference rings appear as concentric circles, while in the centre around the optical axis, depending on the thickness and refractive index of the glass sheet, and particularly depending on the wavelength of the light, a light or dark circular angle region is produced. It is known from the literature that the local transmission maxima of the interference rings in the case of monochromatic light can be described by the following formula:

$$2nd \cos \Phi = m\lambda \quad (1)$$

where n is the group refractive index, d is the thickness of the window, $\Phi$ is the angle with the optical axis, m is the order of interference and $\lambda$ is the wavelength.

If the wavelength of the light beam is now varied continuously, as is necessary when measuring a spectrum, as a rule the total transmitted intensity is continuously modulated accordingly by the angle regions that are to be passed through, as a result of the constructive or destructive interference that varies for each individual angle. In particular, the central region of the ring pattern which appears to pulsate contributes to the amplitude of the modulation. This modulation represents the generally disruptive effect for technical applications, which is reduced according to the present disclosure.

For a perpendicular incidence ($\Phi=0$) the equation for the wavelength distance $\Delta\lambda$ of two modulation maxima is obtained from formula (1) as follows:

$$\Delta\lambda = \frac{\lambda^2}{2nd} \quad (2)$$

which represents the known formula for the spacing of two modes of a Fabry-Perot resonator.

In the literature the resonance spectrum which is periodically structured with $\Delta\lambda$ is partly misleadingly referred to as a "fringe" as well, even though this does not refer to a modulation in the angular space as a reduced representation of the local space, but to a modulation in the wavelength or frequency space.

Figure 2:
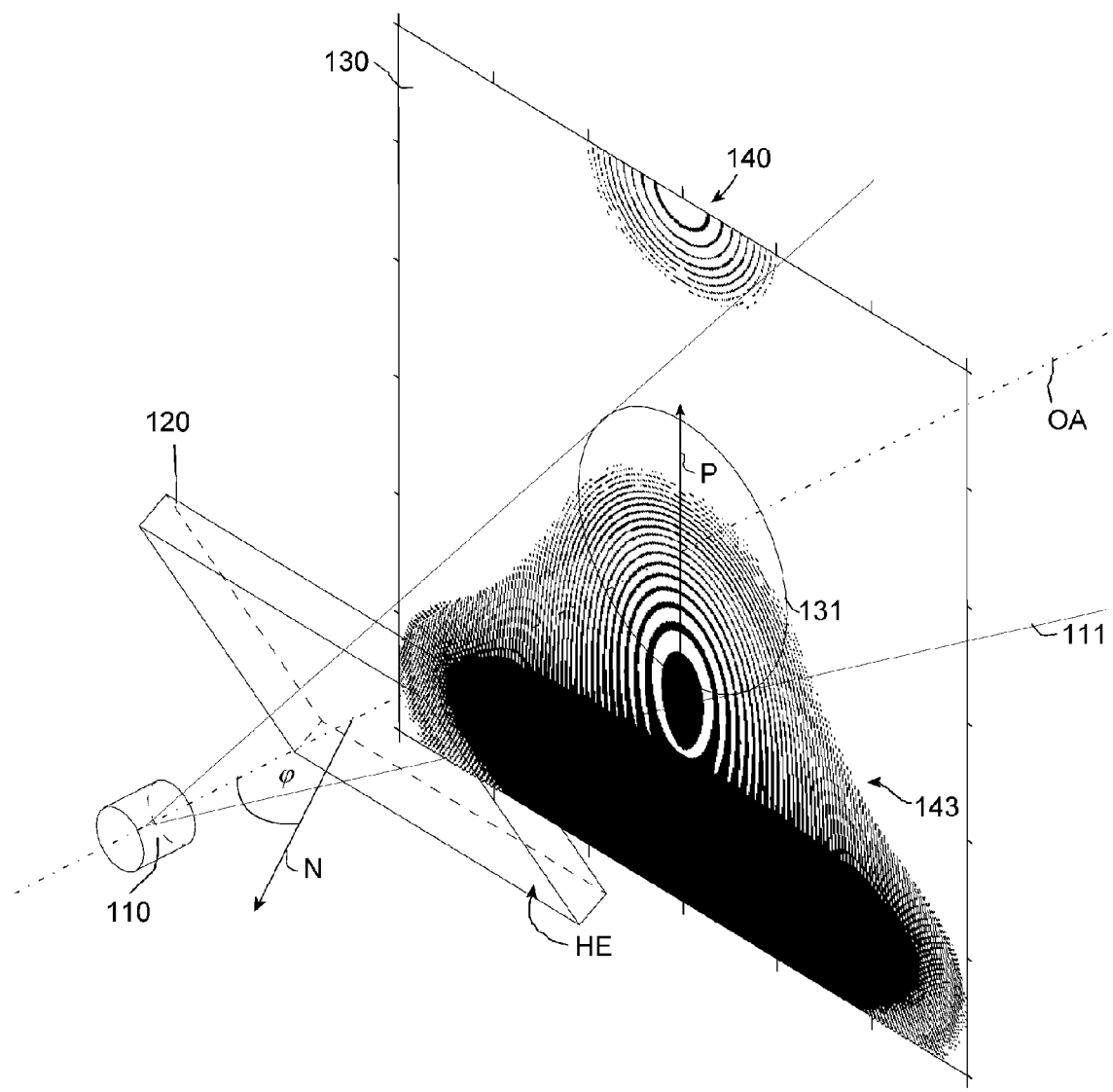
FIG. 2 includes a schematic diagram of a light source, an exit window and the resulting interference pattern when linearly polarised light is diagonally incident at an angle of about 30°.
Figure 3:
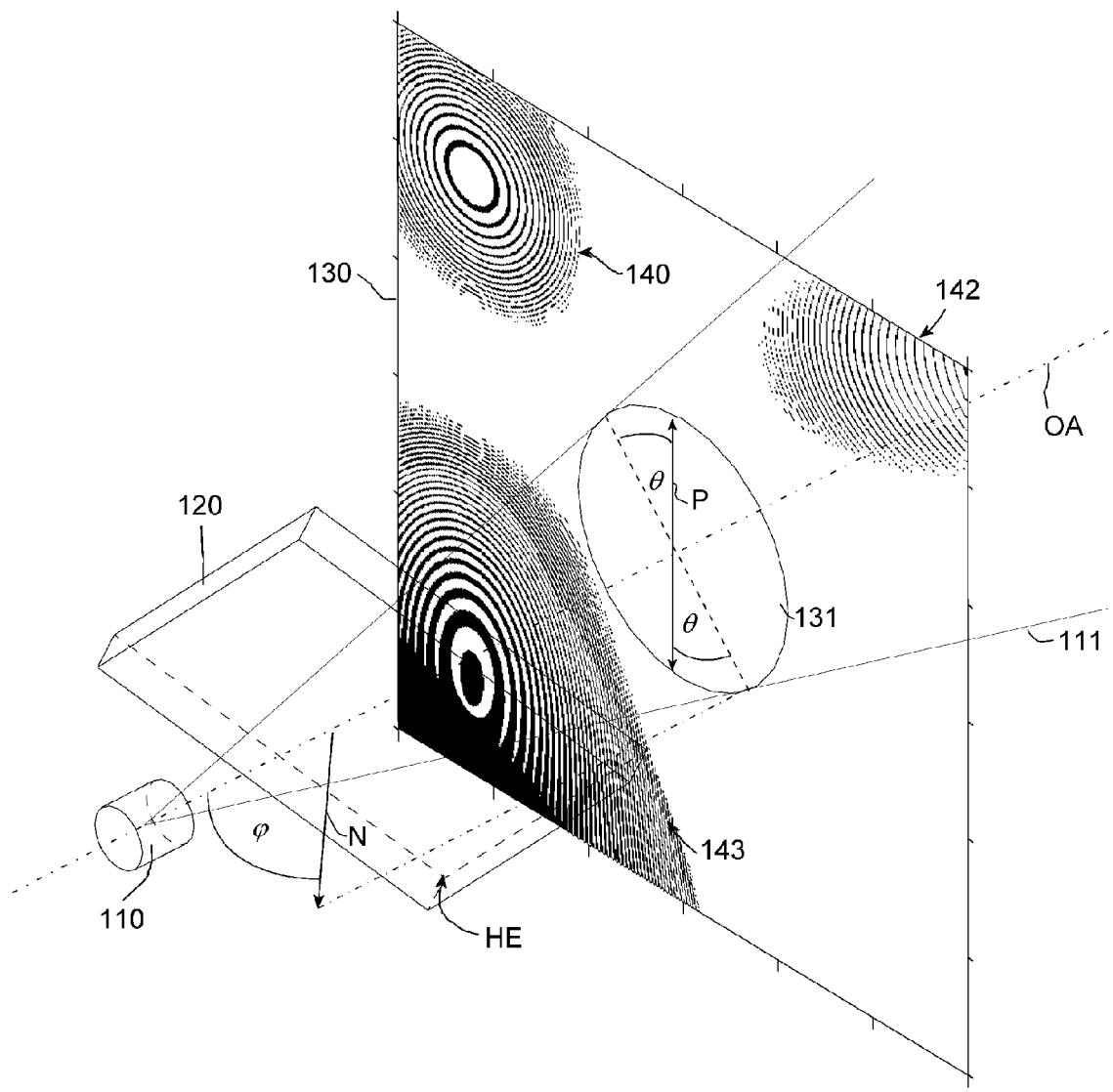
FIG. 3 includes a schematic diagram of a light source and an exit window of a luminous unit and the interference pattern that is produced by the inclined incidence at an angle of about 30° and the s+p polarisation, according to some exemplary embodiments.

The following is a description of FIGS. 1 to 3 in which like elements have been given like reference numerals. FIGS. 1 to 3 show how, starting from a configuration with a perpendicular incidence (FIG. 1), it is possible to arrive stepwise at a configuration according to exemplary embodiments (FIG. 3).

Figure 6:
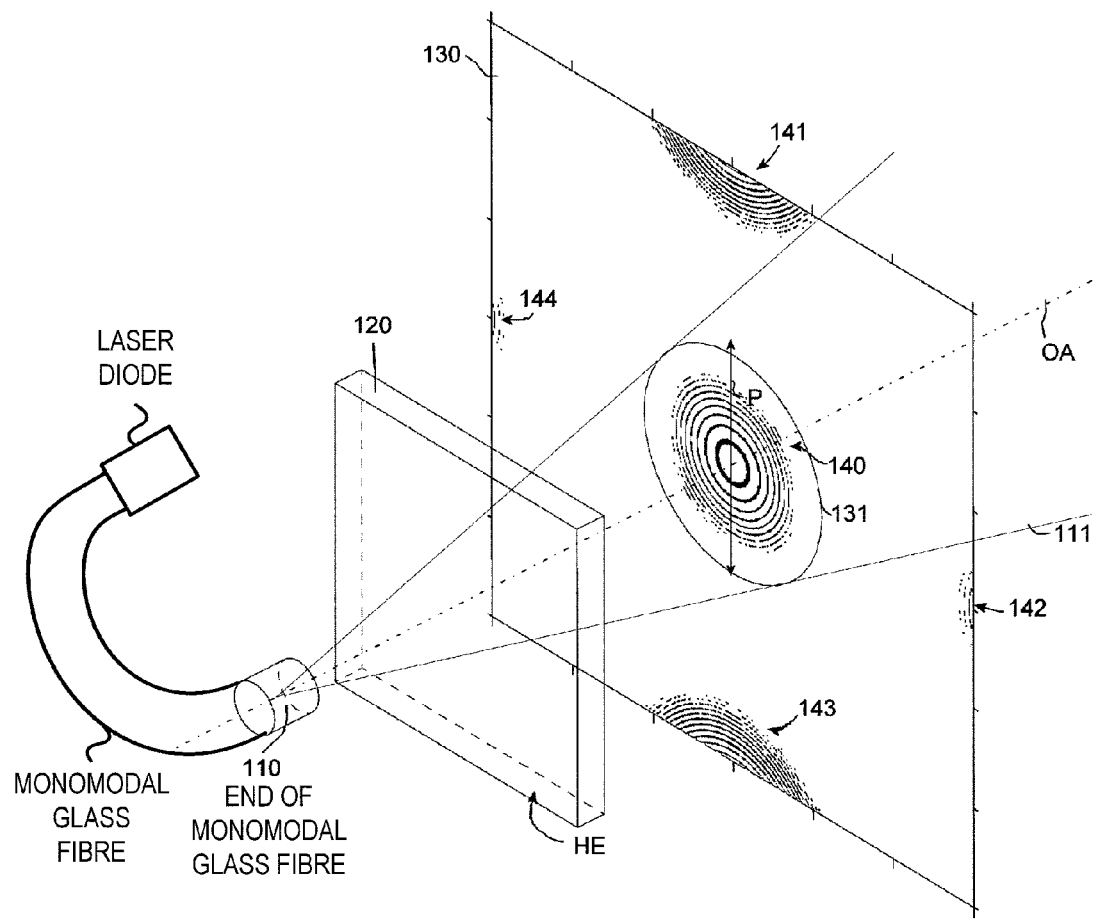
FIG. 6 includes a schematic diagram similar to that of FIG. 1 but where the light source is one end of a monomodal glass fibre emitting light coupled thereto from a laser diode.

With reference to FIG. 1 the interference pattern that is obtained with perpendicularly incident, linearly polarised light will first be described. A light source, which in some exemplary embodiments is a laser diode 110, and can be, in particular, in the form of a vertical-cavity surface-emitting laser (VCSEL), emits linearly polarised, monomodal, approximately monochromatic laser light which impacts, as a divergent light beam 111 with a main emission direction OA, on an exit window 120 with a main extension plane HE. To improve the illustration the divergence of the light radiation 111 is shown in highly exaggerated manner. The wavelength of the laser diode 110 is adjustable or tunable, i.e. variable within conventional limits, for example by controlled variation of the injection current and/or the laser diode temperature. FIG. 6 illustrates an alternate embodiment where the light source is one end of a monomodal glass fibre, which emits light coupled thereto from a laser diode.

The main emission direction OA simultaneously defines the optical axis. The direction of polarisation of the light radiation 111 is marked by an arrow P.

A graphic representation of the interference pattern can be obtained, in particular, by numerical calculation of the electromagnetic field vectors based on the formulae of Airy and Fresnel, the latter being relevant particularly to the quantitative calculation of multi-layer systems, for example windows with an antireflective coating. The interference pattern calculated in this way is shown at some distance behind the exit window in a diagram 130, for illustration purposes. The area actually illuminated is marked by a circle 131 in the diagram 130.

As a result of the polarisation of the light radiation 111, additional concentric angular regions appear, in addition to a central interference pattern 140, as marked partial patterns 141, 142, 143, 144, etc., which are arranged, as a fair approximation, on a cross in the angular space. The cross is oriented by the direction of polarisation P of the incident light radiation 111, so that the axes run parallel and perpendicular to the direction of polarisation. If the incidence is perpendicular the axes intersect on the optical axis.

As a result of the illumination which is effectively limited to the area 131 around the optical axis OA, the transmitted intensity pattern of the light close to the axis resembles that of the unpolarised case.

Because of the invariance of the angular pattern of the interferences in relation to the spacing between the light source 110 or aperture and the window 120, all the alignments of the window 120 relative to the optical axis OA and the direction of polarisation P of the incident beam 111 can be described by an inclination and rotation hereinafter, without any restriction of the generality.

With reference to FIG. 2, this shows how the window 120 is tilted from the position perpendicular to the optical axis OA by an angle of inclination φ, so that the normal N to the main extension plane HE encloses an inclination angle φ, in this case 30°, with the main emission direction OA of the light source 110. The tilt ensures that the cross on which the marked partial patterns 140 etc. are located is displaced relative to the optical axis OA. The alignment of the cross does not rotate and remains aligned with the direction of polarisation P of the incident beam 111. The angular spacings of the marked partial patterns vary relative to the optical axis OA. In particular, the central interference pattern 140 is pushed away from the optical axis OA (upwards, in the figure). In the configuration shown, the direction of polarisation P is located in the plane of incidence that is spanned by N and OA. Thus, there is p-polarisation.

Next, the exit window (and with it its normal N) is rotated about the optical axis OA by a rotation angle θ. The interference pattern which is then produced, according to exemplary embodiments, is shown in FIG. 3. As the light beam and hence the polarisation direction P are retained, there is a rotation of the plane of incidence spanned by N and OA with respect to the direction of polarisation P about the rotation angle θ.

The rotation of the plane of incidence spanned by N and OA with respect to the direction of polarisation P about a rotation angle θ causes further displacement of the cross and hence of the patterns 140, etc. The cross still remains aligned with the direction of polarisation P of the incident beam 111. In the configuration shown the direction of polarisation P encloses a rotation angle θ of 45° with the plane of incidence that is spanned by N and OA. Thus, there is s+p-polarisation.

Overall, the possibility is created of placing the optical axis or main emission direction OA away from the intersecting axes in an intermediate space of the cross. As the effectively limited angular expansion of the incident beam 111 illuminates only an effectively limited part 131 of the total pattern of interferences, the amplitude of the modulation of the total transmitted intensity can be reduced when the wavelengths is varied. On the one hand, the particularly disruptive and relatively large central regions of the partial patterns are scarcely illuminated and on the other hand the outer rings of the partial patterns in the angular space that are important here are located closer together, so as to obtain a technically advantageous averaging effect over the irradiated angular area.

This averaging effect also leads to a particularly advantageous effect with regard to the dimensions of the window thickness. In the case of perpendicular incidence, it follows from formula (2) that the thickness of the window should be as low as possible in order to obtain the largest possible Δλ and thereby smooth out the unwanted modulation in the wavelength range as much as possible.

However, it follows from formula (1) that the density of the interference rings increases in the intermediate spaces of the cross and the attendant favourable averaging effect is associated with a greater window thickness. Greater window thicknesses also prove advantageous during manufacture as the surfaces can be polished to a better standard at little cost. In experiments, a window thickness of 1 mm has proved suitable when using borosilicate glass.

Particularly favourable are configurations in which the rotation angle is 45° or 135° or −45° or −135°. This is described in the literature as an s+p-polarisation of the beam relative to the exit window. As a favourable side effect the light source acquires a degree of freedom for the polarisation. The alignment of the light source with the exit window is invariant in the presence of rotations through 90°. In order to reduce still further the absolute modulation caused by interference in transmission, an antireflective coating which is tailored to s+p-polarisation is advisable.

Moreover, an angle of inclination of 30° has proved particularly advantageous, as in this case, on the one hand, favourable results are observed in terms of the wave-optical properties and on the other hand manufacture does not throw up any particular problems. In the production of window covers for laser diodes in round housings the technical conversion of the windows or window frames is subject to various marginal conditions on account of prescribed housing standards and manufacturing techniques. Consequently, it is not possible to implement just any desired tilting of the window with conventional components such as, for example, cylindrical window glass. However, there is no risk of any problems with a tilt of 30°.

Figure 4:
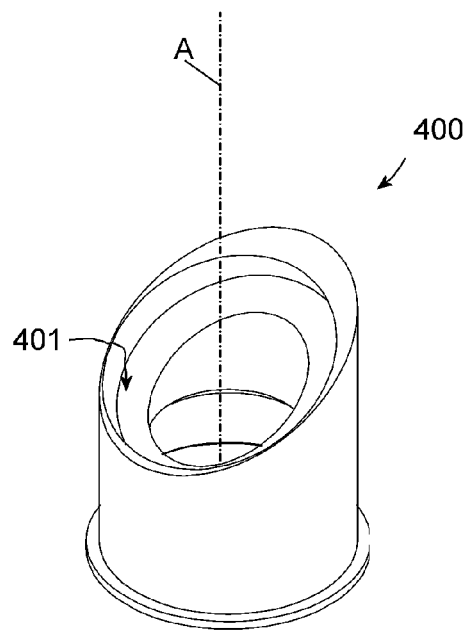
FIG. 4 includes a schematic perspective view of a housing, according to some exemplary embodiments.

FIG. 4 illustrates by way of example a solution with a tilt angle of 30° for standard optical housings. A housing or a cover 400 is embodied here as a round housing with a central axis A, this housing comprising a receptacle 401 for an exit window. The receptacle 401 is provided on the housing 400 so that an angle of inclination φ of, in this case, 30° is formed between the normal to the main extension plane of the window and the main emission direction (in this case the central axis A of the housing). In the alignment of the light source, for example a VCSEL laser diode, this is preferably inserted into the housing so as to obtain an s+p-polarisation as described above. In order to suppress annoying reflections the housing may in particular be internally coated or tinted, particularly tinted black.

Figure 5:
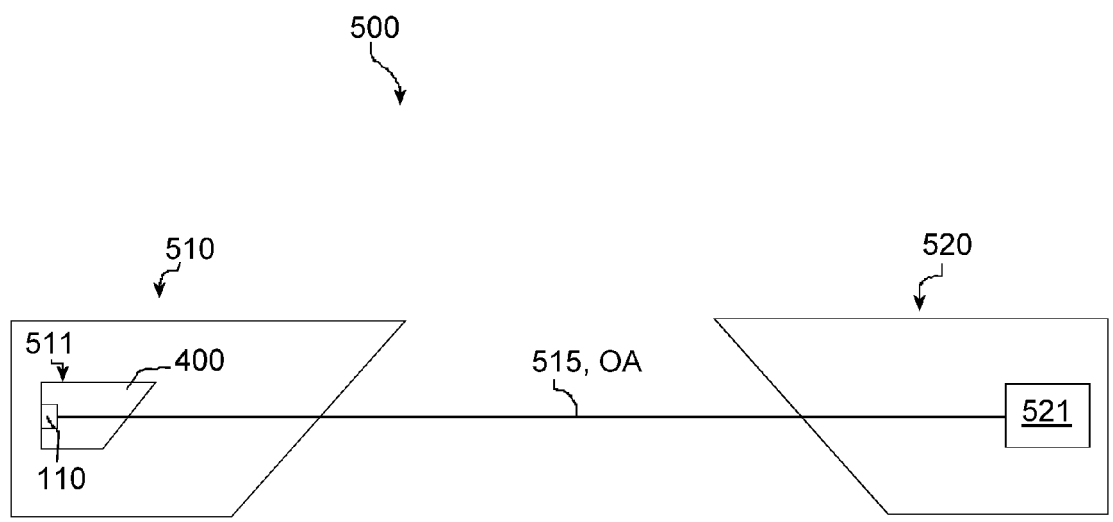
FIG. 5 includes a schematic diagram of a gas sensor, according to some exemplary embodiments.

FIG. 5 illustrates an exemplary embodiment of a gas detector according to the present disclosure in a schematic cross-sectional view, generally designated 500. The gas detector 500 is embodied as an OPGD (Open Path Gas Detector) and comprises a transmitter 510 and a receiver 520.

The transmitter 510 comprises an exemplary embodiment of a luminous unit 511 according to the present disclosure which comprises a light source, in this case in the form of a VCSEL laser diode 110, and a housing 400 according to FIG. 4. The transmitter 510 comprises other elements (not shown), more particularly for actuating and supplying the luminous unit 511.

The luminous unit 511 emits a linearly polarised light radiation 515 in a main emission direction OA which is directed towards the receiver 520.

The receiver 520 comprises a detector 521 for detecting the intensity of the light radiation 515 and other elements (not shown) for supplying and actuating the detector 521.

For further details regarding gas detection background, reference may be made to WO 2005/088275 A1, for example, the entire contents of which are incorporated herein by reference.

While the present disclosure has shown and described exemplary embodiments, it will be understood by those of ordinary skill in the art that various changes in form and details may be made therein without departing from the spirit and scope of the present disclosure, as defined by the following claims.

What is claimed is:

1. A luminous unit for an optical gas detector, comprising:
   a light source for linearly polarised light radiation; and
   a housing with an exit window; wherein:
   a wavelength of the light radiation radiated from the light source is tunable;
   the light source is arranged in the housing such that the main emission direction (OA) of the light source encloses an inclination angle (φ) of between 10° and 50° with a normal (N) to the main extension plane (HE) of the exit window; and
   the light source is oriented about the main emission direction such that the direction of polarisation (P) of the light radiation encloses a rotation angle (θ) of between 22.5° and 67.5° with the plane of incidence on the exit window.

2. The luminous unit according to claim 1, wherein the rotation angle (θ) is between 30° and 60°.

3. The luminous unit according to 1, wherein the rotation angle (θ) is between 35° and 55°.

4. The luminous unit according to claim 1, wherein the rotation angle (θ) is 45°.

5. The luminous unit according to claim 1, wherein the angle of inclination (φ) is between 20° and 40°.

6. The luminous unit according to claim 1, wherein the angle of inclination (φ) is between 25° and 35°.

7. The luminous unit according to claim 1, wherein the angle of inclination (φ) is 30°.

8. The luminous unit according to claim 1, wherein the exit window comprises an antireflective coating for s+p-polarised light.

9. The luminous unit according to claim 1, wherein the exit window has a thickness of at least 0.2 mm.

10. The luminous unit according to claim 1, wherein the exit window has a thickness of at least 1 mm.

11. The luminous unit according to claim 1, wherein the exit window has a thickness of at most 1.5 mm.

12. The luminous unit according to claim 1, wherein the light source is a laser diode.

13. The luminous unit according to claim 1, wherein the light source is a vertical-cavity surface-emitting laser (VCSEL).

14. The luminous unit according to claim 1, wherein the light source is monomodal.

15. The luminous unit according to claim 1, wherein the light source comprises a monomodal laser diode.

16. The luminous unit according to claim 1, wherein the light source comprises a monomodal glass fibre from which monomodal light radiation is emitted.

17. An optical gas detector comprising a luminous unit according to claim 1.

18. A method of recording an absorption spectrum in an optical gas detector according to claim 17, comprising:
   irradiating a volume to be analysed with substantially monochromatic light radiation emitted from the light source, of at least a first wavelength and a second wavelength which differs from the first wavelength; and
   measuring the absorption of the light radiation of the first and second wavelength in the volume that is to be analysed.

* * * * *

UNITED STATES PATENT AND TRADEMARK OFFICE
CERTIFICATE OF CORRECTION

PATENT NO.        : 8,773,663 B2
APPLICATION NO.   : 13/622261
DATED             : July 8, 2014
INVENTOR(S)       : Robert Shau Page 1 of 1

It is certified that error appears in the above-identified patent and that said Letters Patent is hereby corrected as shown below:

In the Claims

Column 8, Line 8, Claim 3, "according to 1" should read --according to Claim 1--.

Signed and Sealed this
Twenty-fourth Day of February, 2015

Michelle K. Lee
*Deputy Director of the United States Patent and Trademark Office*